United States Patent
Sato

(10) Patent No.: US 8,384,402 B2
(45) Date of Patent: Feb. 26, 2013

(54) ANALYSIS TOOL

(75) Inventor: Yoshiharu Sato, Kyoto (JP)

(73) Assignee: Arkray, Inc., Kyoto (JP)

( * ) Notice: Subject to any disclaimer, the term of this patent is extended or adjusted under 35 U.S.C. 154(b) by 393 days.

(21) Appl. No.: 12/740,850

(22) PCT Filed: Oct. 31, 2008

(86) PCT No.: PCT/JP2008/069982
§ 371 (c)(1),
(2), (4) Date: Jun. 18, 2010

(87) PCT Pub. No.: WO2009/057792
PCT Pub. Date: May 7, 2009

(65) Prior Publication Data
US 2010/0244862 A1    Sep. 30, 2010

(30) Foreign Application Priority Data

Oct. 31, 2007 (JP) .................................. 2007-282782

(51) Int. Cl.
*C25B 11/03* (2006.01)
(52) U.S. Cl. .................... 324/692; 204/403.01
(58) Field of Classification Search .......... 324/692, 324/691, 649, 600; 204/400, 403.01, 403.02, 204/403.03, 403.06, 407, 196.06
See application file for complete search history.

(56) References Cited

U.S. PATENT DOCUMENTS

| | | | |
|---|---|---|---|
| 6,562,210 B1 | 5/2003 | Bhullar et al. | |
| 7,455,756 B2 * | 11/2008 | Choi et al. | 204/403.01 |
| 7,928,740 B2 * | 4/2011 | Chung et al. | 324/692 |
| 2001/0021534 A1 * | 9/2001 | Wohlstadter et al. | 436/518 |
| 2004/0005721 A1 | 1/2004 | Tanike | |
| 2004/0040839 A1 | 3/2004 | Yagi | |
| 2004/0140209 A1 | 7/2004 | Choi et al. | |
| 2006/0057436 A1 * | 3/2006 | Osenar et al. | 429/12 |
| 2008/0014631 A1 | 1/2008 | Muraguchi et al. | |

FOREIGN PATENT DOCUMENTS

| | | |
|---|---|---|
| JP | 6-109688 A | 4/1994 |
| JP | 6-281614 | 10/1994 |
| JP | 10-267888 | 10/1998 |
| JP | 2000-241377 | 9/2000 |
| JP | 2001-215215 | 8/2001 |
| JP | 2004-527769 A | 9/2004 |
| WO | 02/35222 | 5/2002 |
| WO | 02/97418 | 5/2002 |
| WO | 2005/069001 | 7/2005 |

* cited by examiner

Primary Examiner — Hoai-An D Nguyen
(74) Attorney, Agent, or Firm — Thomas | Horstemeyer, LLP

(57) ABSTRACT

The present invention relates to an analysis tool including a reagent portion and electrodes. The electrodes include a porous conductive portion where the reagent portion is formed. The porous conductive section is formed by, for instance, coating at least a part of a surface and an inner surface of a porous body with a conductive film. The porous body is, for instance, an insulating fiber mesh cloth. Preferably, the electrodes are formed in a sheet shape.

14 Claims, 7 Drawing Sheets

ANALYSIS TOOL

CROSS REFERENCE TO RELATED APPLICATION

This application is the National Phase of International Application No. PCT/JP2008/069982, filed 31 Oct. 2008, which claims priority to and the benefit of JP patent application number 2007-282782, filed 31 Oct. 2007, the contents of all which are incorporated by reference herein.

TECHNICAL FIELD

The present invention relates to an analysis tool having a reagent portion and electrodes.

BACKGROUND ART

When the glucose concentration of blood is measured, a method of using a disposable analysis tool is being employed as a simple and easy technique. Analysis tools include, for example, an electrode-type biosensor 9 shown in FIGS. 9 and 10 herein (for example, refer to Japanese Patent Application Laid-Open (JP-A) No. 6-109688). This biosensor 9 has electrodes 91 and 92 provided in a substrate 90 and a fluid path 93 for moving a sample such as blood.

The electrode 91 has a reactive electrode 94 for performing transfer of electrons to/from a certain component of blood. The electrode 92 has a counter electrode 95 for generating an electric potential difference from the reactive electrode 94. The reactive electrode 94 and the counter electrode 95 are exposed in the fluid path 93 and also make contact with the reagent portion 96.

In such a biosensor 9, when a voltage is applied between the reactive electrode 94 and the counter electrode 95 while the fluid path 93 is supplied with the sample, a response electric current can be output in response to the concentration of a certain component within the sample. Therefore, in the biosensor 9, it is possible to measure the glucose concentration by measuring the response electric current using the reactive electrode 94 (the electrode 91) and the counter electrode 95 (the electrode 92).

Here, the electrodes 91 and 92 of the biosensor 9 is formed by screen printing using ink containing conductive components such as carbon or silver, metal sputtering, or burying metal pieces in the substrate 90. Therefore, the electrodes 91 and 92 have little or substantially no thickness, and the area of the reactive electrode 94 substantially affect the sensor sensitivity of the biosensor 9. Meanwhile, the biosensor 9 tends to be made to have a smaller size of the fluid path 93 to reduce the necessary amount of the sample and also reduce the areas of the electrodes 91 and 92 and, further, the areas of the reactive electrode 94 and the counter electrode 95. Therefore, when the size of the fluid path 93 is reduced, since the contact area making contact between the sample and the reactive electrode 94 when the fluid path 93 is supplied with the sample tends to be reduced, the output of the biosensor 9 is also reduced, and the sensor sensitivity may be easily dispersed.

In addition, the reagent portion 96 is formed by, for example, attaching a reagent liquid to cover the reactive electrode 94 and/or the counter electrode 95 and drying the reagent liquid. When the reagent liquid is dried, the circumferential portion of the attaching spot is more rapidly dried in comparison with the center portion of the attaching spot of the reagent liquid. Therefore, the circumference of the attaching spot is crystallized first, and the circumference of the reagent portion 96 has a higher concentration of the reagent in comparison with the center portion. As a result, when the reagent portion 96 is dissolved by the sample, the solubility of the reagent portion 96 is degraded, or unevenness in the reagent concentration is generated, so that the measurement accuracy may be degraded. In order to address this problem, since it is necessary to prepare a drying apparatus capable of appropriately controlling environmental conditions such as humidity or temperature, expensive equipment is demanded, and cumbersome efforts is necessary to drive or maintain the apparatus.

Furthermore, when the electrodes 91 and 92 are formed by burying metal pieces in the substrate 90, it is necessary to increase the thickness of the entire substrate. Therefore, when the biosensor 9 is manufactured, it may be impossible to perform a manufacturing process by extracting materials such as the substrate 90 from a roll. In other words, since it is difficult to perform a roll-to-roll manufacturing process, the manufacturing method is limited, and it is difficult to improve the manufacturing efficiency.

DISCLOSURE OF THE INVENTION

Problem to be Solved by the Invention

The present invention has been made to provide an analysis tool such as a biosensor, capable of increasing the electrode area for making contact with the sample, with excellent efficiency and low cost to facilitate miniaturization of the analysis tool.

Means for Solving the Problem

According to the present invention, there is provided an analysis tool including a reagent portion and one or more electrodes, wherein the one or more electrodes include a porous conductive portion where the reagent portion is formed.

The porous conductive potion is obtained by coating a conductive film on at least part of a surface and an inner surface of a porous body. The porous body is, for example, an insulating fiber mesh cloth.

The one or more electrodes are formed to have, for example, a sheet shape. Preferably, the one or more electrodes include a first and second electrode sheet.

The analysis tool according to the present invention may further include an insulating sheet interposed between the first and second electrode sheets. The insulating sheet is, for example, an insulating fiber mesh cloth.

The analysis tool according to the present invention further includes first and second cover sheets between which the first and second electrode sheets are interposed, and the first cover sheet, the first electrode sheet, the insulating sheet, the second electrode sheet, and the second cover sheet are stacked in this order. In this analysis tool, at least one of the first and second cover sheets has a hole for exposing the first and second electrode sheets.

For example, a hole for exposing the first electrode is formed in the first cover sheet, and a hole for exposing the second electrode is formed in the second cover sheet.

In the analysis tool according to the present invention, a hole for exposing the second electrode may be formed in the first cover sheet, the first electrode, and the insulating sheet, and a hole for exposing the first electrode may be formed in the second cover sheet, the second electrode, and the insulating sheet. In this case, the first electrode sheet may be obtained by selectively forming the conductive film on the second cover sheet side of the porous body. Meanwhile, the second electrode may be obtained by selectively forming the conductive film on the first cover sheet side of the porous body.

According to the present invention, a hole for exposing the second electrode may be formed in the first cover sheet, the first electrode, and the insulating sheet, and a hole for exposing the first electrode may be further formed in the first cover sheet.

Preferably, in the analysis tool according to the present invention, a hydrophobic process is performed to surround the circumference of the reagent portion, and a hydrophilic process is performed at a portion where the reagent portion is formed.

BEST MODE FOR CARRYING OUT THE INVENTION

Hereinafter, the present invention is described below with reference the drawings.

First, the first embodiment of the present invention is described below with reference to FIGS. 1 to 4.

Figure 1:
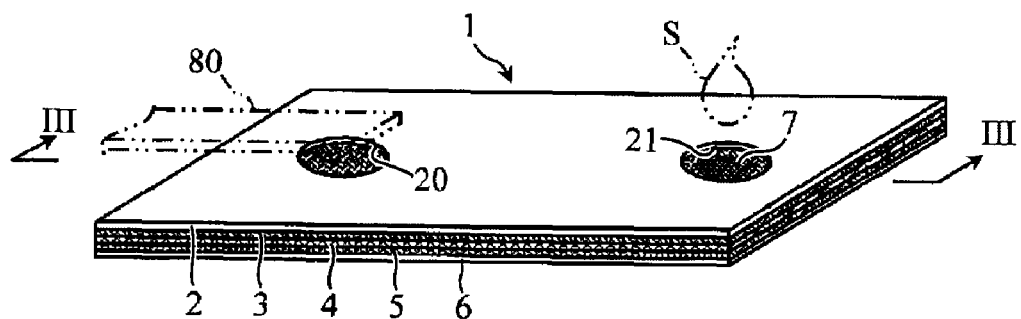
FIG. 1 is a perspective diagram illustrating the entire biosensor according to a first embodiment of the present invention.
Figure 2:
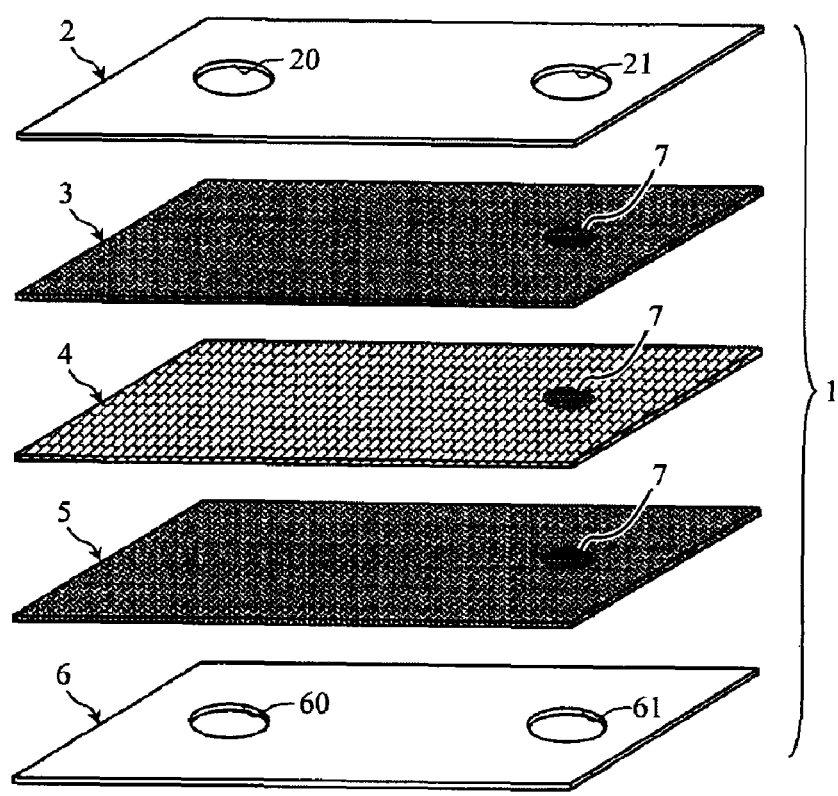
FIG. 2 is an exploded perspective view illustrating the biosensor of FIG. 1.
Figure 3:
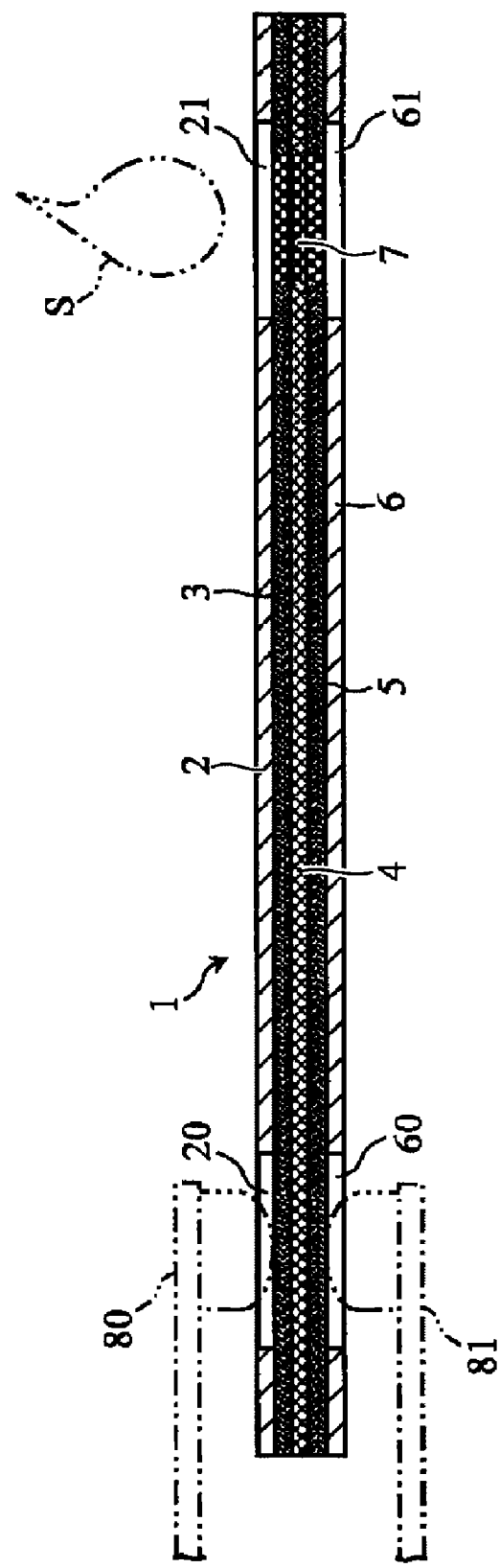
FIG. 3 is a cross-sectional view along a line III-III of FIG. 1.

The biosensor 1 shown in FIGS. 1 to 3 is configured as a disposable type and installed in an analyzer such as a concentration measurement apparatus to analyze a certain component (for example, glucose, cholesterol, or lactic acid) within a sample (for example, a biochemical sample such as blood or urine). The biosensor 1 has a stack structure including a cover sheet 2, an electrode sheet 3, a separator 4, an electrode sheet 5, and a cover sheet 6 and is formed as a sheet shape as a whole. The biosensor 1 also has a reagent portion 7 to allow the analysis of the sample by attaching the sample to the reagent portion 7.

The cover sheets 2 and 6 are provided to protect the electrode sheets 3 and 5 and define an attaching area or a movement area of the sample and have through-holes 20, 21, 60, and 61. The through-holes 20 and 60 are provided to allow the connectors 80 and 81 of the analyzer to make contact with the electrode sheets 3 and 5 and expose a part of the electrode sheets 3 and 5. The through-holes 21 and 61 function as an attaching hole for the sample supplied to the biosensor 1 and an air vent port. The cover sheets 2 and 6 are formed of, for example, an insulating resin material such as PET and have a thickness of 150 to 300 μm.

The electrode sheets 3 and 5 receive voltages by the connectors 80 and 81 of the analyzer and may be formed as a sheet shape having a thickness of, for example, 10 to 50 μm. The electrode sheets 3 and 5 are entirely porous and have conductivity at least on the surface(s). Porosity of the electrode sheets 3 and 5 is set to, for example, 10 to 300 μm with respect to a mesh diameter or a porous diameter such that a capillary force sufficient to move the sample can be acted without generating clogging when the sample is supplied. Such electrode sheets 3 and 5 may be formed by providing a conductive film on the surface of the porous body having low conductivity.

The porous body may include, for example, an insulating fiber cloth. The insulating fiber cloth may be obtained, for example, by plain-weaving an insulating fiber. The insulating fiber may have a fiber length of 5 to 100 μm using, for example, polyethylene or nylon. Needless to say, the insulating fiber cloth may also include other fabrics such as twill or sateen woven fabrics or nonwoven fabrics.

The porous body may include foam or a porous material obtained by integrating plural particles in addition to the fiber cloth.

Meanwhile, the conductive film may be formed on the porous body by, for example, a method of forming a film known in the art using a conductive material such as metal.

The metal material may include, for example, platinum (Pt), gold (Au), palladium (Pd), or nickel (Ni).

The film-forming method may include, for example, sputtering, deposition, or plating.

It is not necessary that the electrode sheets 3 and 5 be entirely formed using a porous body as a base material. Instead, at least a portion where the reagent portion 7 is provided (where the sample is moved) may be porous or the entire body may be porous due to the conductor.

The separator 4 is provided to maintain an insulation state between the electrode sheets 3 and 5, and may be formed as a sheet shape having a thickness of, for example, 10 to 50 μm and entirely porous due to the insulation material. The separator 4 may include a material capable of acting a capillary force sufficient to move the sample without generating clogging when the sample is supplied, and may include, for example, a porous body having a mesh diameter or a porous diameter of 10 to 300 μm. The porous body may include the same porous material as those that can be employed in the electrode sheets 3 and 5.

In addition, the electrode sheets 3 and 5 and the separators 4 are hydrophilically processed in the area where the reagent portion 7 is provided and also hydrophobically processed in the area surrounding at least the circumference of the reagent portion 7. The hydrophilic process may be performed by coating a surfactant such as lecithin or irradiating ultraviolet or vacuum ultraviolet rays. The hydrophobic process may be performed by coating fluorine or the like.

When the reagent portion 7 is formed by performing the hydrophilic process for the area where the reagent portion 7 is formed, it is possible to impregnate a reagent liquid for selectively forming the reagent portion 7 for the hydrophilically processed portion. As a result, it is possible to appropriately define the reagent portion 7. When the reagent portion 7 is supplied with the sample, the sample is actively moved to the hydrophilically processed portion, and it is possible to suppress the sample from penetrating into areas other than the reagent portion 7. Therefore, it is possible to selectively and efficiently supply the sample to the reagent portion 7.

Meanwhile, in the electrode sheets 3 and 5 and the separator 4, it is possible to suppress the sample from penetrating into the circumference of the reagent portion 7 by performing the hydrophobic process to surround the reagent portion 7 when the reagent portion 7 is supplied with the sample. As a result, it is possible to selectively and efficiently supply the sample to the reagent portion 7.

The reagent portion 7 is provided for reaction of the sample and continuously formed along the electrode sheet 3, the separator 4, and the electrode sheet 5 between the cover sheets 2 and 6 and the through-holes 21 and 61. Such a reagent portion 7 contains a reagent such as an oxidoreductase and an electron carrier material and is formed by supporting such a sample within a predetermined area in the electrode sheet 3, the separator 4, and the electrode sheet 5.

The oxidoreductase is selected depending on the type of a certain component within the sample. For example, when glucose is analyzed, glucose oxidase (GOD) or glucose dehydrogenase (GDH) may be used, and typically, PQQGDH is used. The electron carrier material may include, for example, a ruthenium complex or an iron complex, and typically [Ru(NH$_3$)$_6$]Cl$_3$ or K$_3$[Fe(CN)$_6$].

Since the biosensor 1 described above has the reagent portion 7 in the electrode sheets 3 and 5 and the separator 4 formed as a porous material, it is possible to enlarge the contact area between the reagent portion 7 and the sample and the electrode sheet 3 and 5 and the separator 4. As a result, it is possible to improve an output of the biosensor 1 and further sensor sensitivity. In addition, since the reagent portion 7 is formed by supporting the reagent in the porous body, it is possible to increase a solubility of the reagent portion 7 and uniformize the concentration of the sample when the sample is supplied in comparison with a case where the reagent portion is formed in a flat shape as in the related art. Therefore, in the biosensor 1, it is possible to appropriately achieve minimization of the biosensor 1 while appropriately obtaining the measurement accuracy.

Figure 4:
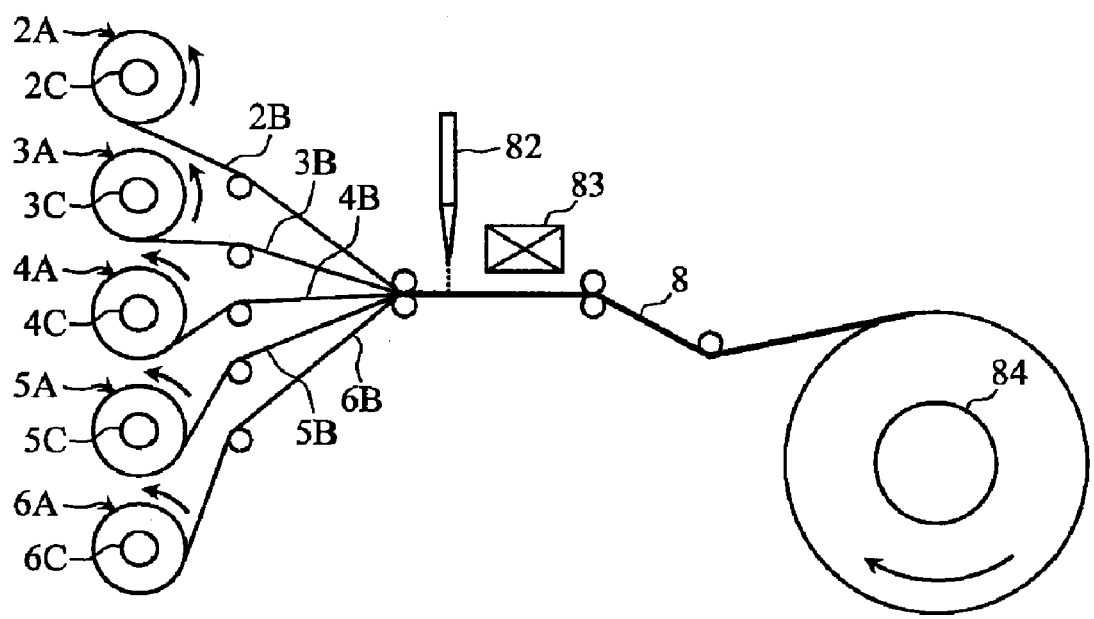
FIG. 4 is a schematic constructional diagram for describing a method of manufacturing the biosensor of FIG. 1.

Next, an exemplary method of manufacturing the biosensor 1 is described below with reference to FIG. 4.

In the manufacturing of the biosensor 1, first, plural material rolls 2A, 3A, 4A, 5A, and 6A are prepared.

The material rolls 2A and 6A become the cover sheets 2 and 6 of the biosensor 1, and have plural through-holes corresponding to the through-holes 20, 21, 60, and 61 of the cover sheets 2 and 6. Such material rolls 2A and 6A are formed by winding long sheets 2B and 6B, for example, having plural through-holes that have been previously formed, around cores 2C and 6C. The long sheets 2B and 6B may be formed of, for example, an insulating resin material such as PET having a thickness of 150 to 300 μm, and the through-holes may be formed by, for example, a punching process.

The punching process for forming plural through-holes may be performed in the same manufacturing line as that of a process of stacking material sheets 2A to 6A or a process of attaching a reagent liquid immediately before the process of stacking the material sheets 2A to 6A.

The material rolls 3A and 5A become the electrode sheets 3 and 5 of the biosensor 1 and have a porous shape having conductivity in at least a part of the surface and the inner surface. Such material sheets 3A and 5A are formed by winding the long sheets 3B and 5B of an insulating fiber cloth having a conductive film having a thickness of, for example, 10 to 50 μm around the cores 3C and 5C. The conductive film may be formed by a film-forming method known in the art using a conductive material such as metal.

The material roll 4A becomes the separator 4 of the biosensor 1 and has a porous shape. The material roll 4A is formed by winding the long sheet 4B of an insulating fiber cloth having a thickness of, for example, 10 to 50 μm around the core 4C.

In the long sheets 3B to 5B, as necessary, a hydrophilic process is performed for the area where the reagent portion 7 is previously provided (the area corresponding to predetermined through-holes of the long sheets 2B and 6B), and a hydrophobic process is entirely or partially performed so as to enclose the hydrophilically processed portion. The hydrophilic process is performed by, for example, a surfactant process or irradiating ultraviolet rays, and the hydrophobic process is performed by, for example, a fluorine coating process.

Next, the material rolls 2A to 6A are set, and the long sheets 2B to 6B are stacked to each other by pulling out the long sheets 2B to 6B from the material rolls 2A to 6A. In this case, bonding layers are formed between the neighboring long sheets to provide a stack sheet 8. The bonding layers may be formed by interposing bonding sheets such as a double-sided adhesive tape or a hot-melt bonding sheet between the long sheets 2A to 6A. After stacking the long sheets 2B to 6B, the long sheets 2B to 6B are bonded to each other through a compression bonding or a thermal compression bonding.

Next, a reagent liquid is attached on predetermined through-holes of the long sheet 2B. The reagent liquid contains an oxidoreductase and an electron carrier material and is attached by a dispenser 82 known in the art. Here, since the long sheets 3B to 5B are formed of a porous material, the reagent liquid attached through the through-holes is penetrated into the long sheets 3B to 5B. Therefore, since the reagent liquid is uniformly dried in comparison with a case where the reagent liquid is attached on a flat surface, it is possible to uniformize the reagent concentration when the sample is supplied to the reagent portion 7 and the reagent portion 7 is dissolved.

By performing the hydrophilic process for the positions of the long sheets 3B to 5B corresponding to the through-holes of the long sheet 2B, it is possible to selectively penetrate the reagent liquid into the hydrophilically-processed portion when the reagent liquid is attached through the through-holes of the long sheet 2B. Furthermore, since it is possible to suppress the reagent liquid from penetrating into the circumference of the hydrophilically-processed area by performing the hydrophobic process around the hydrophilically-processed area, it is possible to more selectively penetrate the reagent liquid into the hydrophilically-processed portion.

Then, after the reagent liquid is dried using a drying unit 83 such as a heater or air blower as necessary, the stack sheet 8 is wound around the core 84. Finally, the biosensor 1 shown in FIGS. 1 to 3 can be obtained by performing a punching process or a cutting process for the stack sheet 8. In addition, the punching or cutting of the stack sheet 8 may be performed in the same manufacturing line as that of the process of coating the reagent liquid before the stack sheet 8 is wound around the core 83.

As such, since the biosensor 1 can be formed using plural material rolls 2A to 6A, it is possible to perform, a so-called roll-to-roll manufacturing. Therefore, it is possible to manufacture the biosensor 1 in an efficient and inexpensive manner with few limitations.

Figure 5:
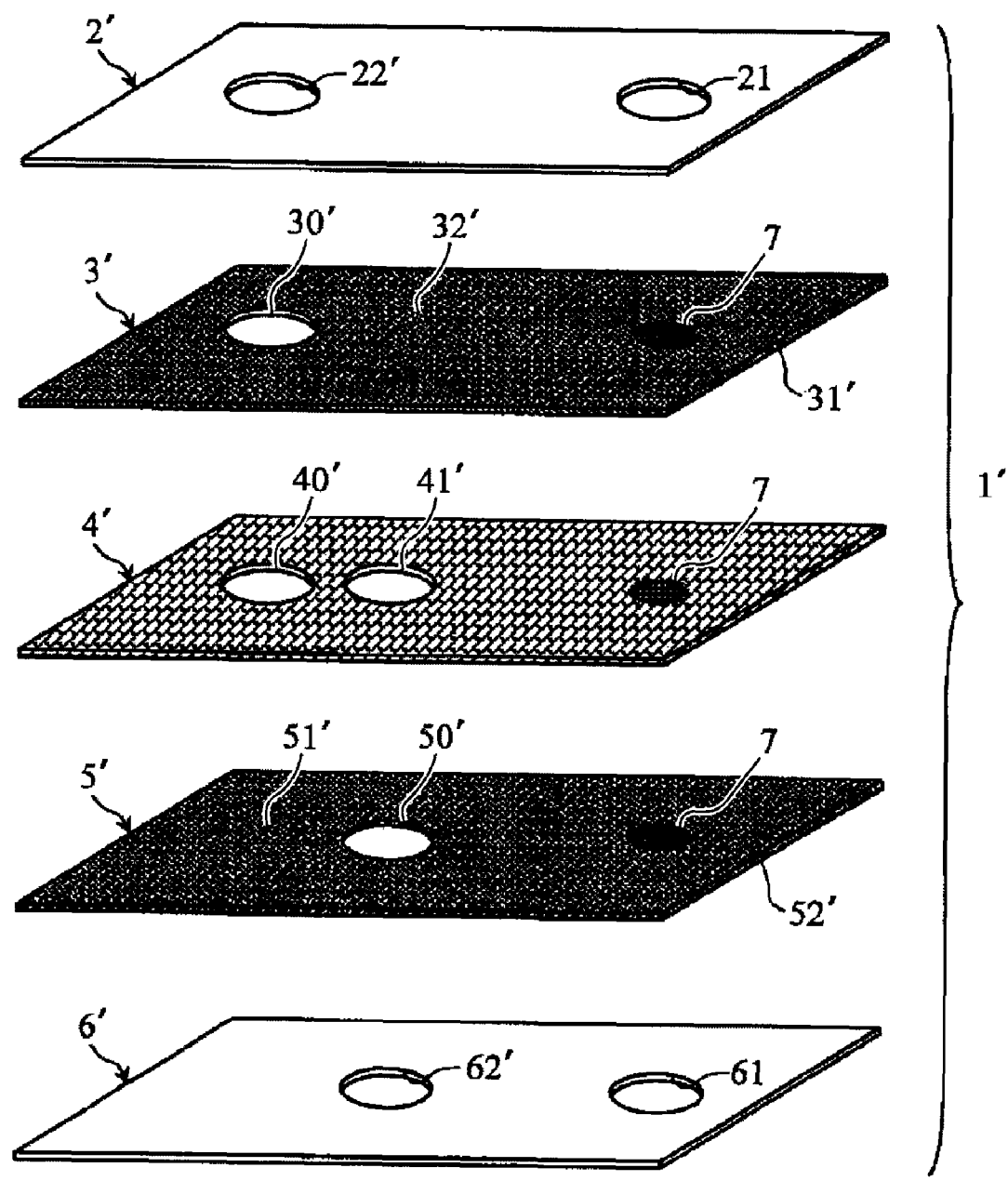
FIG. 5 is an exploded perspective diagram illustrating the biosensor according to a second embodiment of the present invention.
Figure 6:
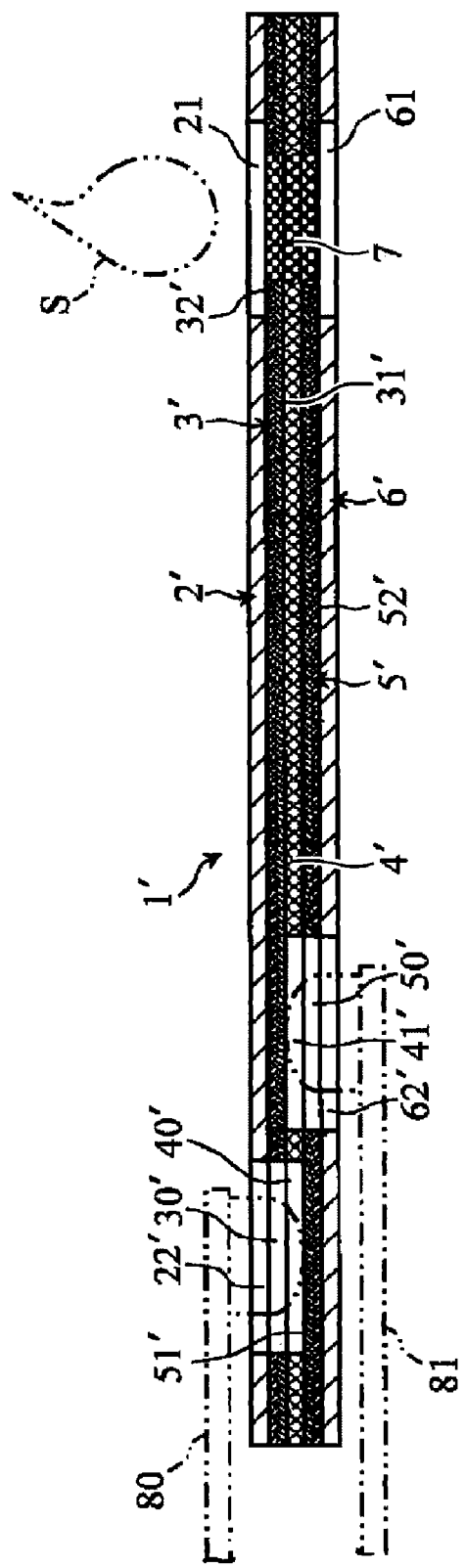
FIG. 6 is a cross-sectional view corresponding to FIG. 3 illustrating the biosensor of FIG. 5.

Next, the biosensor according to the second embodiment of the present invention is described below with reference to FIGS. 5 and 6. In FIGS. 5 and 6, like reference numerals denote like elements as in the first embodiment of the present invention described above, and repetitive descriptions thereof are omitted hereinafter.

The biosensor 1' shown in FIGS. 5 and 6 is formed as a sheet shape obtained by stacking a cover sheet 2', an electrode sheet 3', a separator 4', an electrode The cover sheet 2', the electrode sheet 3', and the separator 4' have through-holes 22', 30', and 40', respectively, communicating with one another. The through-holes 22', 30', and 40' are provided to expose the electrode sheet 5' and allow the connector 80 to make contact with the electrode sheet 5'.

The separator 4', the electrode sheet 5', and the cover sheet 6' have through-holes 41', 50', and 62', respectively, communicating to one another. The through-holes 41', 50', and 62' are provided to expose the electrode sheet 3' and allow the connector 81 to make contact with the electrode sheet 3'.

In the electrode sheets 3' and 5', surfaces 31' and 51', where the separator 4' is bonded to, selectively have conductivity. In other words, since the electrode sheets 3' and 5' make contact with the connectors 80 and 81, respectively, on the surfaces 31' and 51', it is not necessary to actively conduct the surfaces 32' and 52'. Such electrode sheets 3' and 5' may be provided by forming a conductive film on only a single surface of the porous body such as an insulating fiber cloth.

Needless to say, the electrode sheets 3' and 5' may be obtained by forming a conductive film on all of the surfaces 31' and 51' and the surfaces 32' and 52'. Alternatively, the electrode sheets 3' and 5' may be obtained by forming a conductive film on predetermined portions including an area where the reagent portion 7 is formed and an area making contact with the connectors 80 and 81.

Since the area where the reagent portion 7 is formed is also porous in the biosensor 1', it is possible to increase the contact area between the reagent portion 7 or the sample and the electrode sheets 2' and 4' or the separator 3'. As a result, it is possible to improve the output of the biosensor 1' and further the sensor sensitivity. It is possible to appropriately prepare miniaturization of the biosensor 1' while appropriately obtaining the measurement accuracy.

Figure 7:
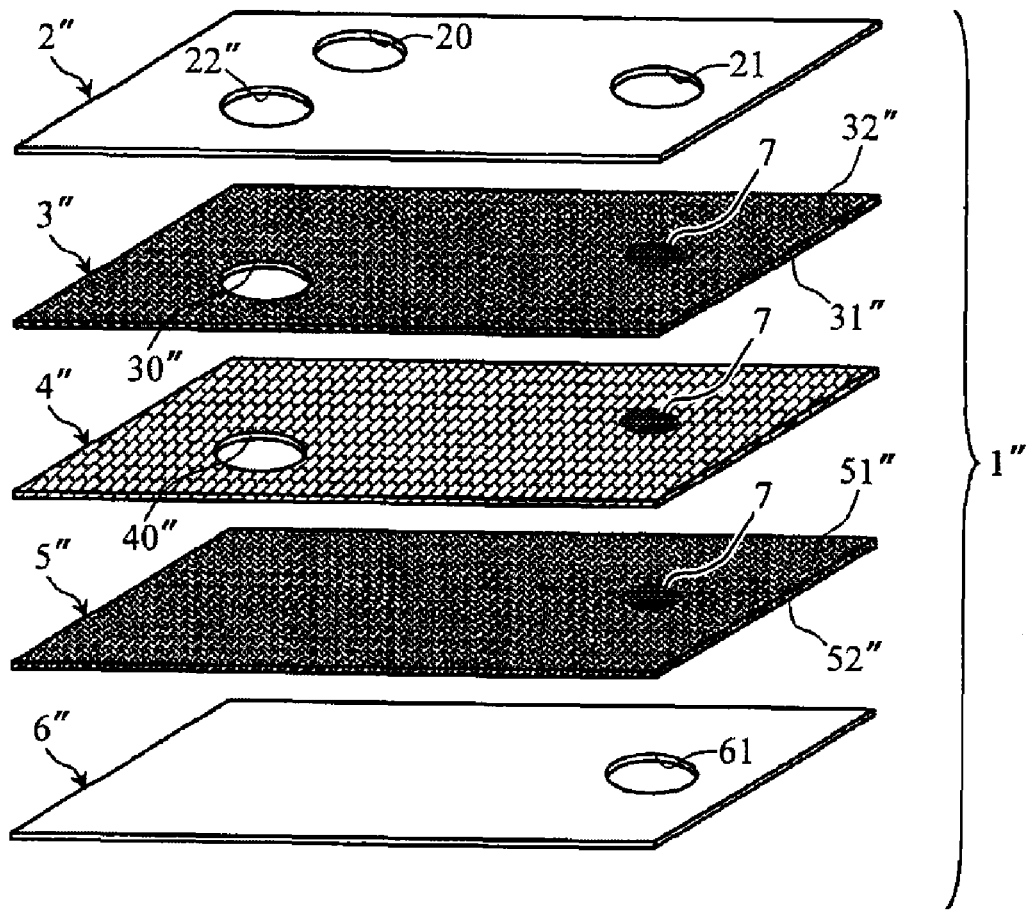
FIG. 7 is an exploded perspective diagram illustrating the biosensor according to a third embodiment of the present invention.
Figure 8:
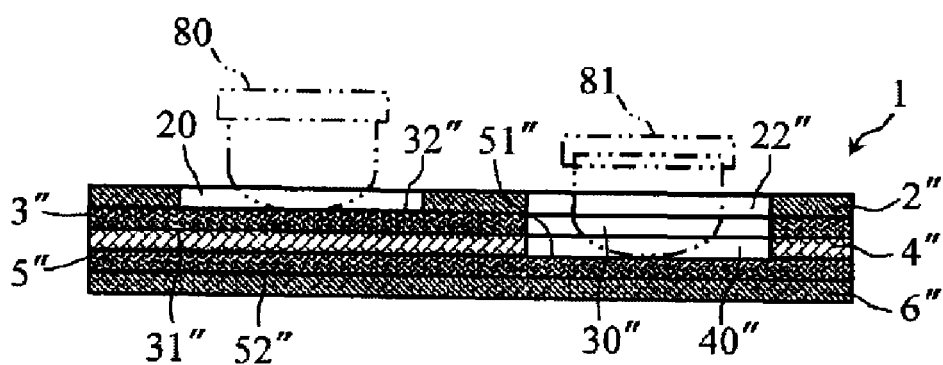
FIG. 8 is a cross-sectional view corresponding to FIG. 3 illustrating the biosensor of FIG. 7.
Figure 9:
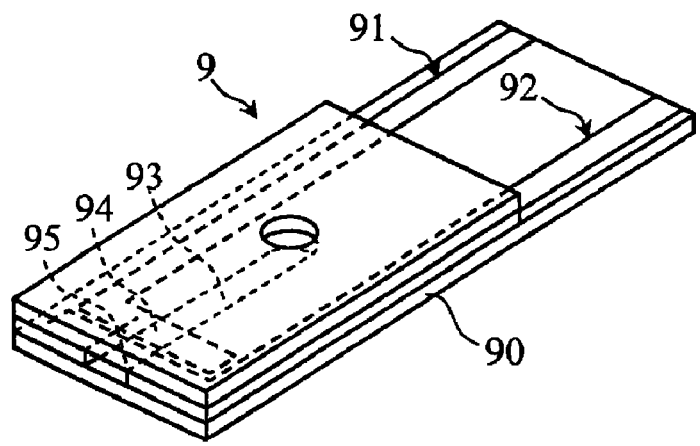
FIG. 9 is a perspective diagram illustrating the entire biosensor as an example of the analysis tool of the related art.
Figure 10:
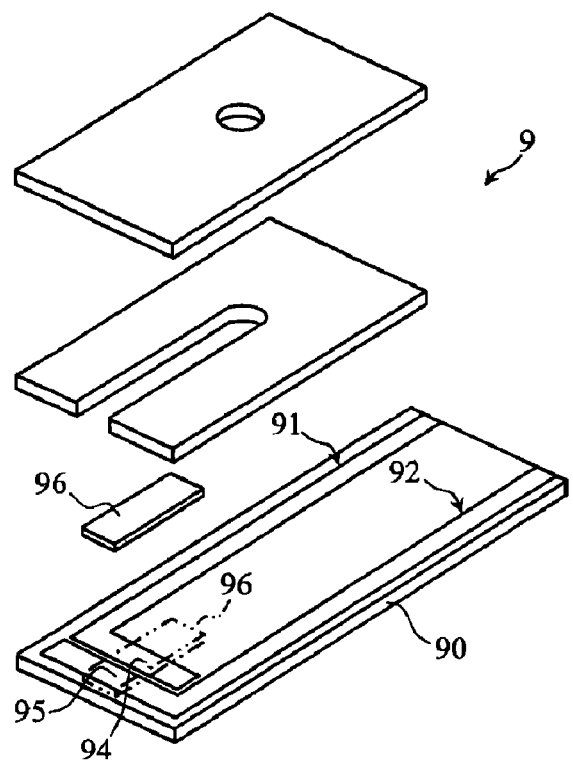
FIG. 10 is an exploded perspective diagram illustrating the biosensor of FIG. 9.

Next, the biosensor according to the third embodiment of the present invention is described below with reference to FIGS. 7 and 8. In FIGS. 7 and 8, like or substantially identical elements are denoted by like reference numerals as in the first embodiment described above, and repetitive descriptions thereof are omitted hereinafter.

The biosensor 1" shown in FIGS. 7 and 8 has a sheet shape obtained by stacking a cover sheet 2", an electrode sheet 3", a separator 4", an electrode sheet 5", and a cover sheet 6".

The cover sheet 2", the electrode sheets 3", and the separator 4" have through-holes 22", 30", and 40", respectively, communicating with one another. The through-holes 22", 30", and 40" are provided to expose the electrode sheet 5" and allow the connector 81 to make contact with the electrode sheet 5".

Meanwhile, the electrode sheet 3" is exposed by the through-hole 20 of the cover sheet 2". As a result, the connector 80 is allowed to make contact with the electrode sheet 3". That is, the electrode sheets 3" and 5" are exposed through the cover sheet 2". Therefore, in the analyzer, the connectors 80 and 81 are arranged side by side in the cover sheet 2" side.

The electrode sheet 3" is arranged such that the surface 32" opposite to the surface 31", where the separator 4" is bonded, selectively has conductivity. The electrode sheet 5" is arranged such that the surface 51", where the separator 4" is bonded, selectively has conductivity. That is, since the electrode sheets 3" and 5" make contact with the connectors 80 and 81 on the surfaces 32" and 51", respectively, it is not necessary to actively conduct the surfaces 31" and 52". Such electrode sheets 3" and 5" are formed to have porosity by forming a conductive film on only a single surface of a porous body such as an insulating fiber cloth. In addition, the separator 4" may be omitted when the conductivity is selectively provided to the surfaces 32" and 51", and a sufficient insulation can be obtained in the surfaces 31" and 52".

Needless to say, in the electrode sheets 3" and 5", a conductive film may be formed on all of the surfaces 31" and 51" and the surfaces 32" and 52". Alternatively, the conductive film may be formed on predetermined portions including the area where the reagent portion 7 is formed or the area making contact with the connectors 80 and 81.

Also in such a biosensor 1", since the area where the reagent portion 7 is formed has porosity, it is possible to increase the contact area between the reagent portion 7 or the sample and the electrode sheets 2" and 4" and/or the separator 3". As a result, it is possible to improve the output of the biosensor 1" and further the sensor sensitivity. It is possible to prepare minimization of the biosensor 1" while appropriately obtaining the measurement accuracy.

The present invention may be variously modified without limitation to the aforementioned embodiments. For example, the through-holes formed on the cover sheet may be formed as a hole continuously extending to the edge of the cover sheet.

In addition, the number of electrode sheets in the biosensor is not necessarily two, but may include a correction electrode sheet for measuring the influence quantity of the hematocrit in the biosensor, for example, using whole blood as the sample. In addition, the electrode is not necessarily formed as a sheet shape, but may be appropriately designed.

The invention claimed is:

1. An analysis tool comprising:
a reagent portion;
one or more electrodes, the one or more electrodes including first and second electrode sheets; and
an insulating sheet interposed between the first and second electrode sheets,
wherein the first and second electrode sheets each include a porous conductive portion and a hole in the conductive portion, the reagent portion formed in the hole in the porous conductive portion of each of the first and second electrode sheets, and the insulating sheet includes a hole exposing the reagent portion formed in the hole in the conductive portion of the first electrode sheet to the reagent portion formed in the hole in the conductive portion of the second electrode sheet.

2. The analysis tool according to claim 1, wherein the porous conductive potion is obtained by coating a conductive film on at least part of a surface and an inner surface of a porous body.

3. The analysis tool according to claim 2, wherein the porous body is an insulating fiber mesh cloth.

4. The analysis tool according to claim 1, wherein the one or more electrodes are formed to have a sheet shape.

5. The analysis tool according to claim 1, wherein a hydrophilic process is performed at a portion where the reagent portion is formed.

6. The analysis tool according to claim 1, wherein the insulating sheet is an insulating fiber mesh cloth.

7. The analysis tool according to claim 1, further comprising first and second cover sheets between which the first and second electrode sheets are interposed,
wherein the first cover sheet, the first electrode sheet, the insulating sheet, the second electrode sheet, and the second cover sheet are stacked in this order, and at least one of the first and second cover sheets has a hole for exposing the first and second electrode sheets.

8. The analysis tool according to claim 7, wherein
a hole for exposing the first electrode sheet is formed in the first cover sheet, and
a hole for exposing the second electrode sheet is formed in the second cover sheet.

9. The analysis tool according to claim 1, wherein a hydrophobic process is performed to surround a circumference of the reagent portion.

10. An analysis tool comprising:
a reagent portion; and
one or more electrodes,
wherein the one or more electrodes include a porous conductive portion where the reagent portion is formed, the one or more electrodes formed to have a sheet shape;
wherein the one or more electrodes include first and second electrode sheets, and the analysis tool further comprises an insulating sheet interposed between the first and second electrode sheets;
the analysis tool further comprising first and second cover sheets between which the first and second electrode sheets are interposed,
wherein the first cover sheet, the first electrode sheet, the insulating sheet, the second electrode sheet, and the second cover sheet are stacked in this order, and
at least one of the first and second cover sheets has a hole for exposing the first and second electrode sheets; and
wherein a hole for exposing the second electrode sheet is formed in the first cover sheet, the first electrode sheet, and the insulating sheet, and
a hole for exposing the first electrode sheet is formed in the second cover sheet, the second electrode sheet, and the insulating sheet.

11. The analysis tool according to claim 10, wherein
the porous conductive portion is obtained by coating a conductive film on at least part of a porous body,
the first electrode sheet is obtained by selectively forming the conductive film on a second cover sheet side of the porous body, and
the second electrode sheet is obtained by selectively forming the conductive film on a first cover sheet side of the porous body.

12. The analysis tool of claim 10, wherein the reagent portion is formed within the porous conductive portion.

13. An analysis tool comprising:
a reagent portion; and
one or more electrodes,
wherein the one or more electrodes include a porous conductive portion where the reagent portion is formed, the one or more electrodes formed to have a sheet shape;
wherein the one or more electrodes include first and second electrode sheets, and the analysis tool further comprises an insulating sheet interposed between the first and second electrode sheets;
the analysis tool further comprising first and second cover sheets between which the first and second electrode sheets are interposed,
wherein the first cover sheet, the first electrode sheet, the insulating sheet, the second electrode sheet, and the second cover sheet are stacked in this order, and
at least one of the first and second cover sheets has a hole for exposing the first and second electrode sheets; and
wherein a hole for exposing the second electrode sheet is formed in the first cover sheet, the first electrode sheet, and the insulating sheet, and
a hole for exposing the first electrode sheet is further formed in the first cover sheet.

14. The analysis tool of claim 13, wherein the reagent portion is formed within the porous conductive portion.

* * * * *

UNITED STATES PATENT AND TRADEMARK OFFICE
CERTIFICATE OF CORRECTION

PATENT NO.       : 8,384,402 B2
APPLICATION NO. : 12/740850
DATED            : February 26, 2013
INVENTOR(S)      : Yoshiharu Sato It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 442 days.

Signed and Sealed this
First Day of September, 2015

Michelle K. Lee
*Director of the United States Patent and Trademark Office*